(12) United States Patent
Volkau et al.

(10) Patent No.: US 12,279,860 B2
(45) Date of Patent: Apr. 22, 2025

(54) HAND-EYE COORDINATION RELATED GAMING SYSTEMS AND METHODS

(71) Applicants: Aliaksandr Volkau, Starye Dorogi (BY); Victar Laurentsyeu, Minsk Region (BY)

(72) Inventors: Aliaksandr Volkau, Starye Dorogi (BY); Victar Laurentsyeu, Minsk Region (BY)

(*) Notice: Subject to any disclaimer, the term of this patent is extended or adjusted under 35 U.S.C. 154(b) by 536 days.

(21) Appl. No.: 17/844,287

(22) Filed: Jun. 20, 2022

(65) Prior Publication Data

US 2023/0052750 A1 Feb. 16, 2023

Related U.S. Application Data

(60) Provisional application No. 63/229,110, filed on Aug. 4, 2021.

(51) Int. Cl.
*A61B 5/11* (2006.01)
*A61B 5/00* (2006.01)
*A63B 22/00* (2006.01)
*A63F 13/00* (2014.01)

(52) U.S. Cl.
CPC .......... *A61B 5/1124* (2013.01); *A61B 5/7475* (2013.01); *A63B 22/00* (2013.01); *A63F 13/00* (2013.01); *A63B 2022/0092* (2013.01)

(58) Field of Classification Search
None
See application file for complete search history.

(56) References Cited

U.S. PATENT DOCUMENTS

| 7,052,392 | B2 | 5/2006 | Tessmer et al. |
| 9,123,209 | B2 | 9/2015 | Pacey et al. |
| 2002/0010013 | A1 | 1/2002 | Walker et al. |
| 2019/0130548 | A1* | 5/2019 | Biswas ............... G06T 5/40 |
| 2020/0320781 | A1* | 10/2020 | Tran ................... A61B 5/742 |
| 2024/0104873 | A1* | 3/2024 | Pastrana Vicente .. G06F 3/0482 |

* cited by examiner

*Primary Examiner* — Ronald Laneau
(74) *Attorney, Agent, or Firm* — Nath, Goldberg & Meyer; Joshua B. Goldberg (57) ABSTRACT

A gaming system according to some aspects of the invention includes a processor, and a memory device storing a plurality of instructions, when executed by the processor, cause the processor to cause a display, by a display device, of a first shape having a first location and a movable second shape having an initial location. The processor receives, player commands for dimensional change the second shapes, after which the second shape moves towards the first shape. The processor causes temporal dimensional changes of the first shape. At least one part of the second shape fits into at least one part of the first shape, at least in one temporary occurrence where the dimensions of the first shape and the second shape allow said fit. The processor checks whether the second shape reached the first shape and whether, if the second shape reached the first shape location, there exists a fit.

16 Claims, 11 Drawing Sheets

HAND-EYE COORDINATION RELATED GAMING SYSTEMS AND METHODS

RELATED APPLICATIONS/PRIORITY CLAIMS

This application claims the benefit under 35 USC 119(e) and 120 of U.S. Provisional Application No. 63/229,110 filed Aug. 4, 2021, and which is incorporated herein by reference.

TECHNICAL FIELD

The present invention relates to gaming, more particularly, the invention relates to systems and methods for gaming, related to hand-eye coordination and response time.

BACKGROUND

Hand-eye coordination is the synchronization of eye and hand movements. It is the ability of the central nervous system to coordinate the information received from the eyes to control, guide, and direct the hands in the accomplishment of a given task. It involves proprioception (knowing where your body is in space) combined with processing visual input. Any task that requires the coordination of vision and hand movements involves hand-eye coordination. Examples of hand-eye coordination include grasping objects, catching and throwing a ball, playing an instrument while reading music, reading and writing, or playing a video game. Hand-eye coordination is a complex neurological process. The eyes send visual information to the brain, which in turn integrates the data and turns them into a three-dimensional image. Two systems help the brain accomplish this task: The focal system identifies the object, and the ambient system that identifies the object's position in space. Once the information is processed, the cerebellum, located in the hindbrain, controls the motor coordination responsible for the task. Developing hand-eye coordination may result in better reaction times. According to some research, developing hand-eye coordination may enhance other life skills, and even strategic thinking. Some research suggests that hand-eye coordination practice may mitigate hand-eye coordination decreases with age. According to some studies with children there exists a correlation between better hand-eye coordination and superior reading, writing, math skills, and better interpersonal communication. The challenge of hand-eye coordination increases especially when it comes to an unexpectedly changing environment. One possible arena where changing conditions can be generated is in gaming. An example of this can be found in the U.S. Pat. No. 7,052,392 which describes, among other things, a possibility in which competitors can change features during the game assisting them in winning their opponents. For example, a bonus game may be implemented in the form of a basketball game wherein the player may elect to lower the hoop, have longer legs, shrink the ball when he is shooting, enlarge the hoop when he is shooting, etc. Similarly, with a hockey game, the size of an opponent's goal may be caused to grow during a match or the size of a player's goal to shrink, or the opposing goaltender's stick to shrink during a match or a player's stick to enlarge. Thus, the player may utilize an advantage selection to initially reduce the size of his own goal, increase the size of his opponent's goal, increase the size of his goal tender's stick, decrease the size of his opponent's goal tender's stick, or reduce the rate at which his goal grows or his goaltender's stick shrinks.

Still there is always an ongoing need for new games, and preferably more sophisticated and challenging ones to satisfy the need for entertainment and challenge of the players.

The terms "first shape", "target", "passive shape" and "passive ring" may be used interchangeably hereinafter.

The terms "shape" and "object" may be used interchangeably hereinafter.

The terms "second shape", "movable object", "thrown object" and "active ring" may be used interchangeably hereinafter.

The terms "player", "competitor" and "user" may be used interchangeably hereinafter.

The terms "match" and "fit" may be used interchangeably hereinafter.

The terms "check" and "test" may be used interchangeably hereinafter.

The term "display" being referred to herein may include virtual and/or augmented reality.

SUMMARY OF EMBODIMENTS OF THE INVENTION

The present invention is aimed to address the ever-existing demand for new games, preferably more sophisticated and challenging to satisfy the need for entertainment and to challenge players.

A gaming system according to some aspects of the present invention includes a processor, and a memory device that stores a plurality of instructions that, when executed by the processor, cause the processor to cause a display, by one or more display devices, of at least one first shape having a first location and at least one movable second shape having an initial location. The processor receives, through at least one input device, one or more player commands for dimensional change of one or more second shapes, after which the second shape moves towards the first shape. The processor causes temporal dimensional changes of the first shape. These temporal dimensional changes of the first shape, can be at random time intervals. At least one part of the second shape fits into at least one part of the first shape, at least in one temporary occurrence where the dimensions of the first shape and the second shape allow said fit. The processor checks whether said second shape reached said first shape and whether, if the second shape reached the first shape location, there exists a fit. According to some embodiments of the present invention, a fit is defined within an allowable range. For example, if the two shapes are square, according to one possible example, a sufficient fit is that the difference in the length of the wigs of the two squares is not more than 1% of the length of the shorter wig and so on. At least one of the first shape, and the second shape, may include at least one empty inner zone. At least one of the first shapes, and the second shapes, may be three dimensional.

According to some embodiments the processor is adapted to allow communication among a plurality of players and the processor, to provide a group gaming environment. In some embodiments, the first shape of one or more players is the second shape for one or more other players. In another example, the second shape of one or more players is the first shape for one or more other players.

A method of operating a gaming system according to some aspects of the invention includes causing a processor which causes at least one display device to display at least one first shape, the shape having a first location; causing the processor to cause at least one display device to display at least one second shape, the second shape having an initial location; and receiving, through at least one input device, at least one player command for dimensional change of the second shape, after which the second shape moves towards the first shape. The processor causes temporal dimensional changes of the first shape. These temporal dimensional changes of the first shape, can be at random time intervals. At least one part of the second shape fits into at least one part of the first shape, at least in one temporary occurrence where the dimensions of the first shape and the second shape allow this fit. The processor checks whether the second shape reached the first shape, and whether if the second shape reached the first shape location there exists a fit. The processor provides an award for each time this fit occurs. In some embodiments of the invention the first and/or the second shapes include one or more empty inner zones. The first and/or the second shapes may be three dimensional.

According to some examples embodying the invention the processor allows communication among a number of players and processor, to provide a group gaming environment. In some embodiments, the first shape of one or more players is the second shape for one or more other players. In another example, the second shape of one or more players is the first shape for one or more other players.

BRIEF DESCRIPTION OF DRAWINGS

Preferred embodiments, features, aspects and advantages of the present invention are described herein in conjunction with the following drawings:

FIGS. 9A-D illustrate schematically a game according to some embodiments of the invention that involves the spatial matching of an enzyme with a substrate.

DETAILED DESCRIPTION OF EMBODIMENTS

Eye-hand coordination is the ability of the central nervous system to coordinate the information received from the eyes to control, guide, and direct the hands in the accomplishment of a given task such as throwing a ball and writing, or playing a video game. Developing hand-eye coordination may result in better reaction times. The challenge of hand-eye coordination increases especially when it comes to an unexpectedly changing environment. The present invention is aimed to address the ever-existing demand for new games, preferably more sophisticated and challenging to satisfy the need for entertainment and to challenge players.

Figure 1A:
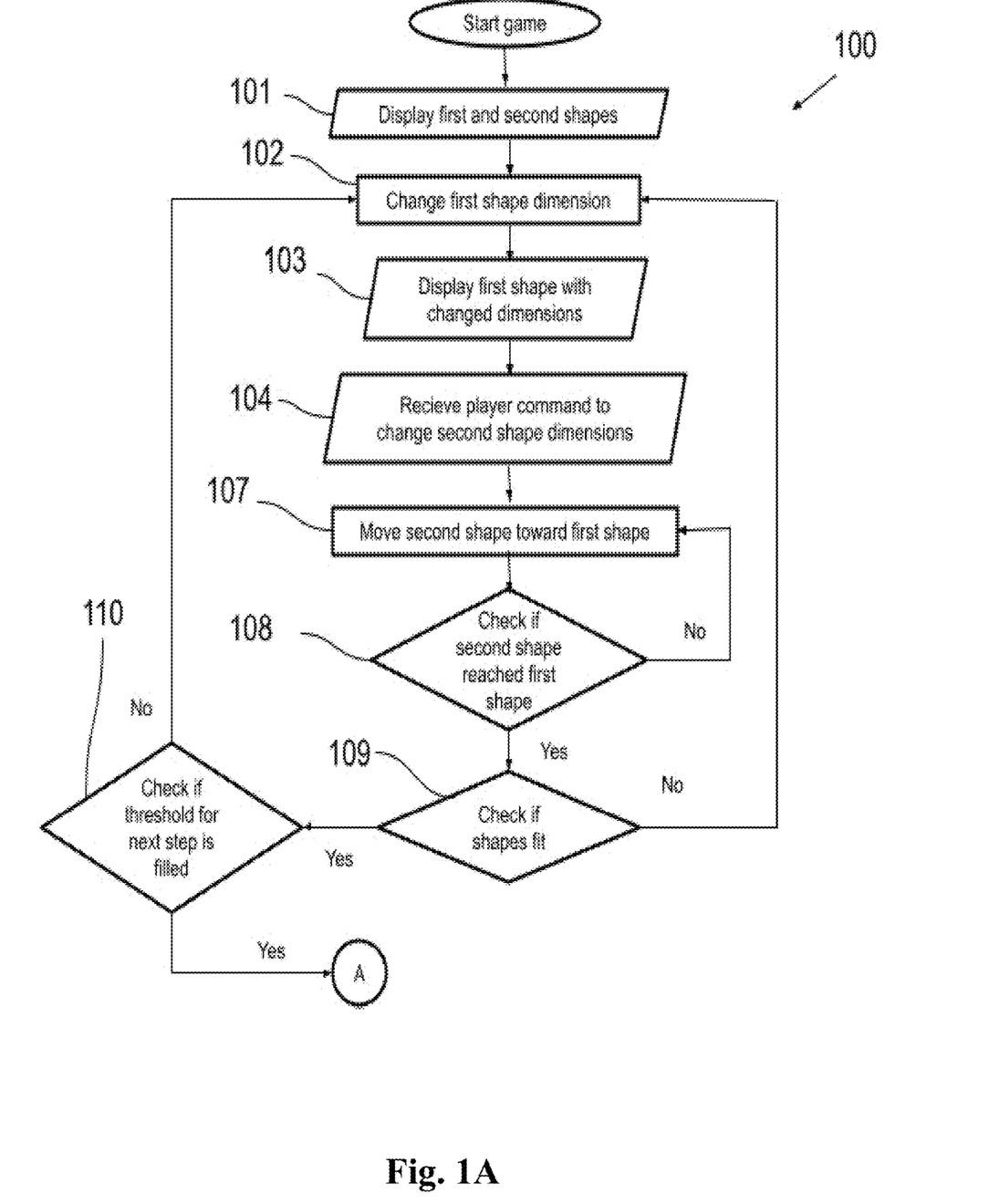
FIGS. 1A-C are flowcharts of processes for operating a gaming system with three difficulty levels according to some embodiments of the present invention where the game starts in level one (low difficulty) shown in FIG. 1A, and the next stages with higher difficulty level are depicted in FIG. 1B and in FIG. 1C.
Figure 1B:
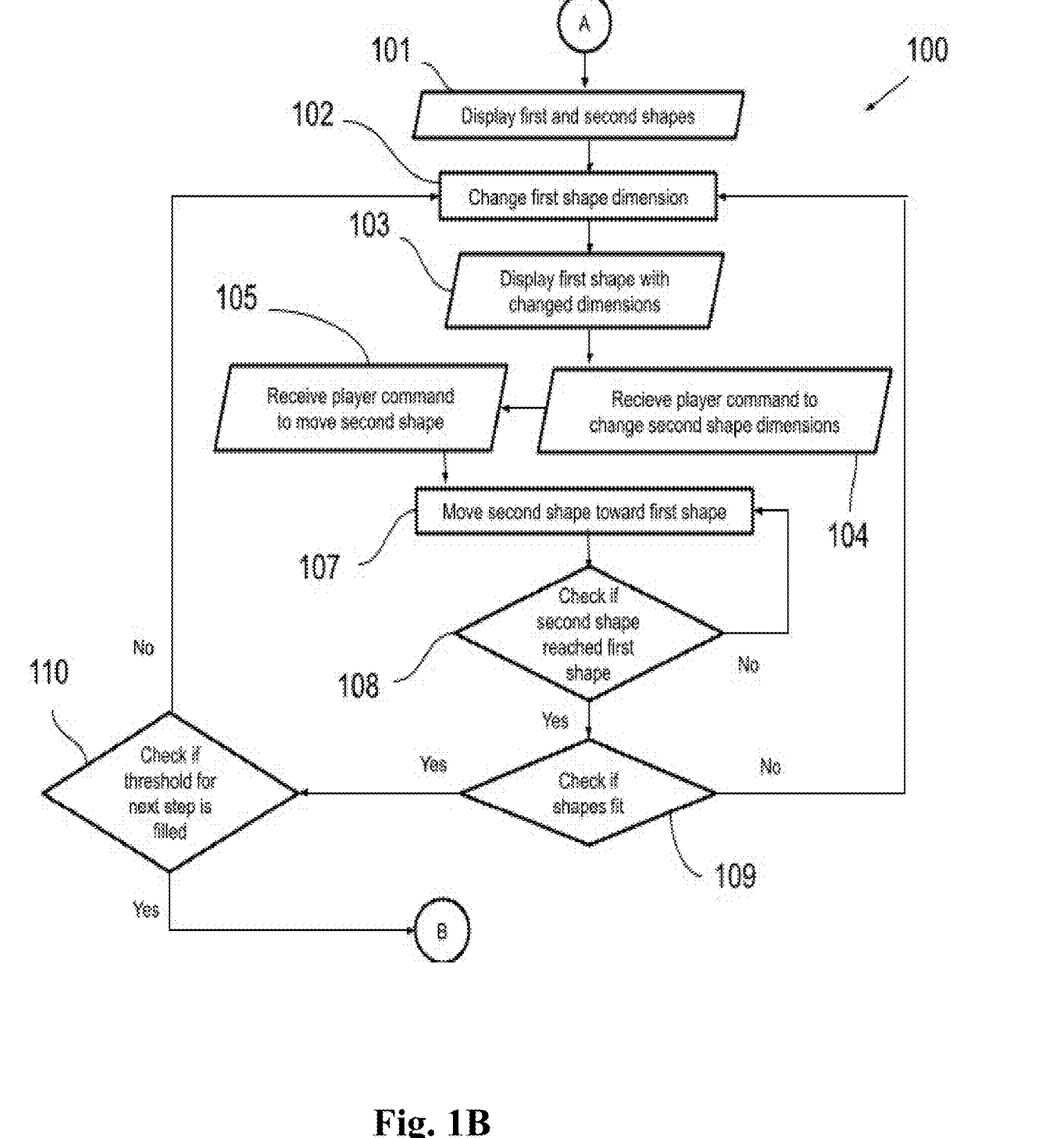
Figure 1C:
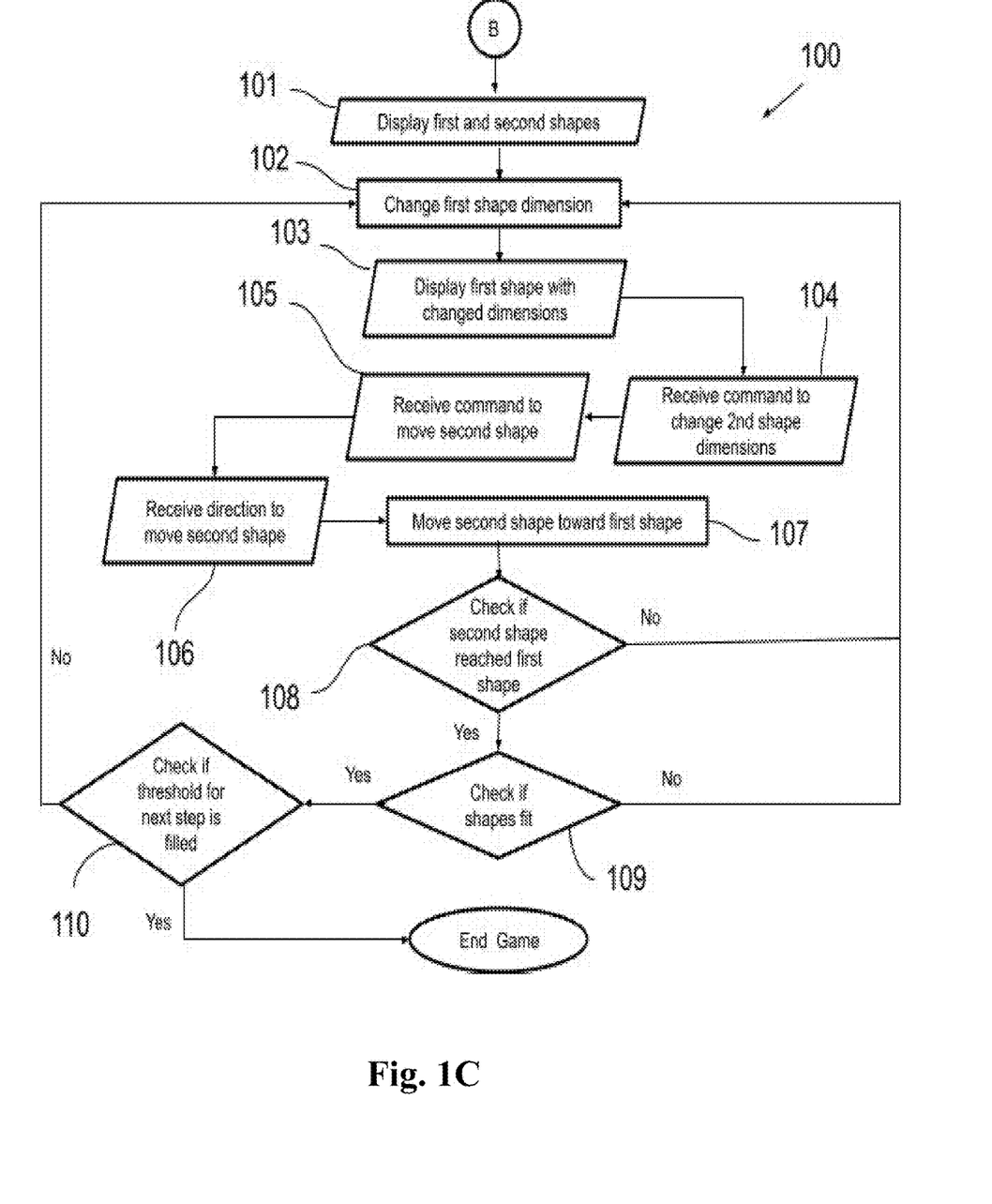

A gaming system according to some aspects of the present invention includes a processor, and a memory device that stores a plurality of instructions that, when executed by the processor, cause the processor to cause a display, by one or more display devices, of at least one first shape having a first location and at least one movable second shape having an initial location. The processor receives, through at least one input device, one or more player commands for dimensional change of one or more second shapes, after which the second shape moves towards the first shape. The processor causes temporal dimensional changes of the first shape. The length of time between each change in shape dimensions can be fixed or random. At least one part of the second shape fits into at least one part of the first shape, at least in one temporary occurrence where the dimensions of the first shape and the second shape allow said fit. The processor checks whether said second shape reached the first shape and whether, if the second shape reached the first shape location, there exists a fit. The processor may provide an award for each time a fit occurs. According to some embodiments of the present invention, a fit is defined within an allowable range. For example, a condition of a fit can be that at least one wig in the two shapes should be similar enough. For example, if the two shapes are square, according to one possible example, a sufficient fit is that the difference in the length of the wigs of the two squares is not more than 1%, or 5%, or 10% of the length of the shorter wig and so on. At least one of the first shape, and the second shape, may include at least one empty inner zone. At least one of the first shapes, and the second shapes, may be three dimensional. The movement of the second shape can occur by itself immediately upon receipt of input for changing the dimensions of the second shape from the player, or this movement will occur only after input of additional command from the player. The player may be required to direct the second shape's movement toward the first shape. According to some examples, the game is divided into difficulty levels according to which, at the low difficulty level, the second shape movement does not require further action on the part of the player after receipt of a player command input to change second shape dimensions. At the higher difficulty level of the game, the player is required to initiate the movement of the second shape, and/or to set the direction of the second shape movement, that is to aim the movement of the second shape towards the first shape. According to some examples, the difficulty level for the whole game can be selected at the beginning. According to other examples, the difficulty level automatically changes to a higher level depending on the score the player receives at the prior lower-level stage. The rapprochement between the two shapes can be the result of a relative movement between the two shapes. That is both the first shape and the second shape may move at the same time. This may increase the challenge of driving the second shape so that it reaches the first shape. The input from the player can be typing, pressing a button, touching the screen, voice, thought, gesture, and facial expression utilizing systems/modules adapted to detect such input. Game 100 according to some embodiments of the invention with three difficulty levels is depicted in the flowcharts in FIGS. 1A-C. Game 100 starts in level one (low difficulty) shown in FIG. 1A. Display 101 appears of the two shapes: a first and a second. Change in the dimensions of the first shape 102, every period of time, starts. Display 103 of the first shape appears after each time its dimensions are resized. Input 104 from the player to change the dimensions of the second shape is received. Then movement 107 of the second shape towards the first form takes place. Two checks are made by the processor: test (check) 108 whether the second shape has reached the first shape, and test (check) 109 whether the two forms are fit. As long as the second shape has not reached the first shape, movement 107 of the second shape continues towards the first shape. If in check 109 it is found that the shapes do not match, the game returns to stage 102 when the first shape changes its dimensions while waiting for the second shape to arrive. If according to test 109 a match was found between the shapes, test 110 is performed as to whether the threshold conditions for the transition to the next stage at a higher level of difficulty of the game have been met. For example, checking the score received by the player calculated by the processor which can include the number of times a match between the shapes was achieved. The score may also include consideration of the time it took the player to reach a match between the shapes. That means a higher score will be given to the player if he or she was able to achieve a match quickly. According to some examples, the player may be rewarded for each time a match between shapes is achieved or whenever the player manages to qualify for a higher game level. Matching (fitting) speed can be calculated in various ways. For example, according to the total time it took to reach the threshold condition for transition to a next (higher) level of the game, or in another example, the total time during which the current stage of the game took divided by the number of times a match between the shapes was achieved. The next stage in the game in the example described in FIG. 1B is conducted in a similar way to the stage described in FIG. 1A in the difference that in order for the second shape to start moving, input 105 should be received from the player. The next stage in the game is shown in FIG. 1C. This stage is quite similar to the stage shown in FIG. 1B, however, an additional input 106 is required from the player to direct movement 107 of the second shape towards the first shape. Therefore, test 108 will only be performed when the player has finished driving the second form, and if it is found that the second shape has not reached the first shape, the game returns to stage 102 where the first shape continues to change in size from time to time and waits for the second shape to arrive. That is, to the stage before the resizing of the second shape by the player and movement 107. If in check 109 it is found that the shapes do not match, the game returns to stage 102 when the first shape changes its dimensions while waiting for the second shape to arrive. If the threshold required to complete the third stage is filled in rest 110, the game ends.

Figure 2A:
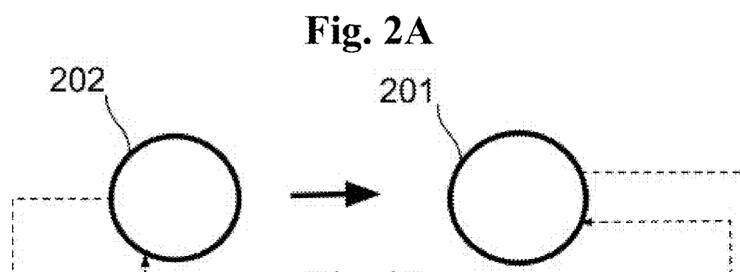
FIGS. 2A-C illustrate schematically a game and a schematic block diagram according to some embodiments of the invention where two separate game shapes are shown in FIG. 2A; where in FIG. 2B one shape encircles another; and a corresponding modular logical structure, is schematically depicted in FIG. 2C FIGS. 3A-B illustrate schematically a game according to some embodiments of the invention where two separate game shapes are shown in FIG. 3A; where in FIG. 3B one shape encircles the other
Figure 2B:
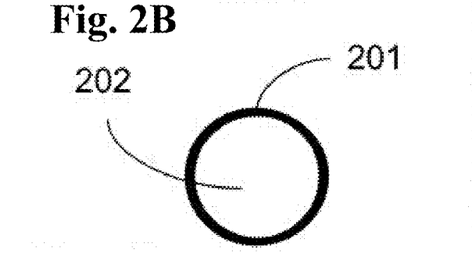
Figure 2C:
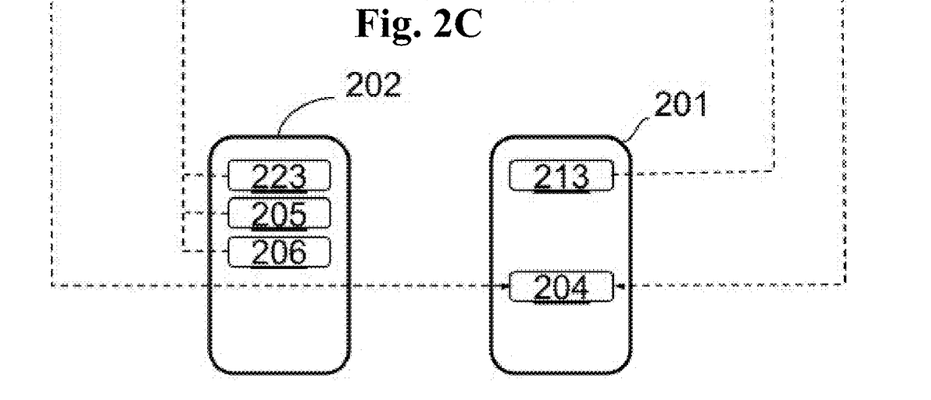
Figure 3A:
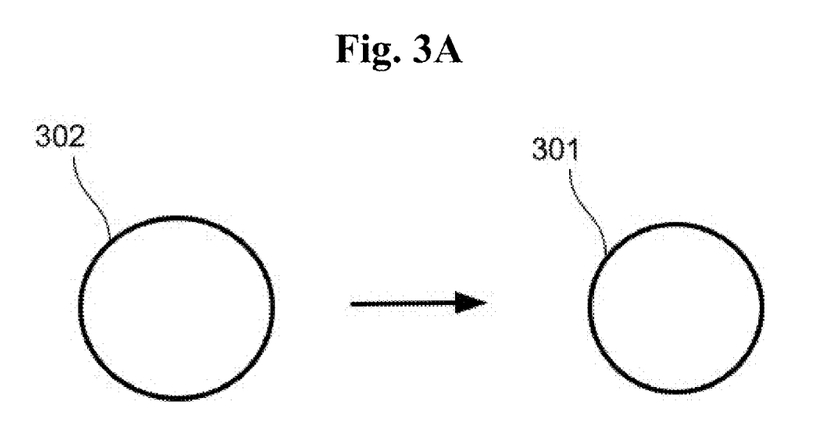
Figure 3B:
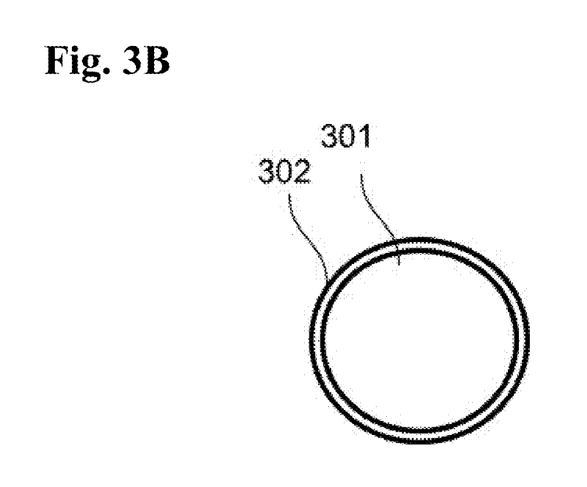
Figure 4A:
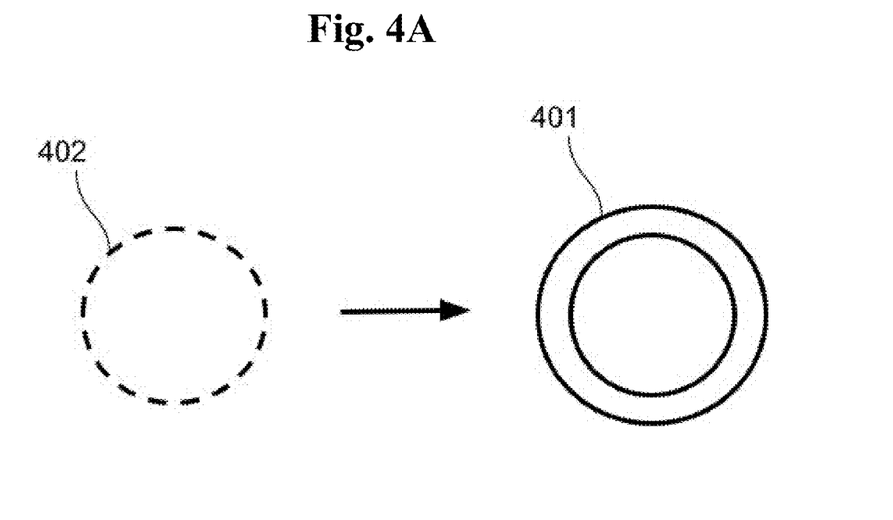
FIGS. 4A-B illustrate schematically a game according to some embodiments of the invention with two shapes, one is a circle and the other consists of two concentric circles, where the two shapes are shown separated in FIG. 4A; while in FIG. 4B the circle shape is placed between the two concentric circles of the other shape.
Figure 4B:
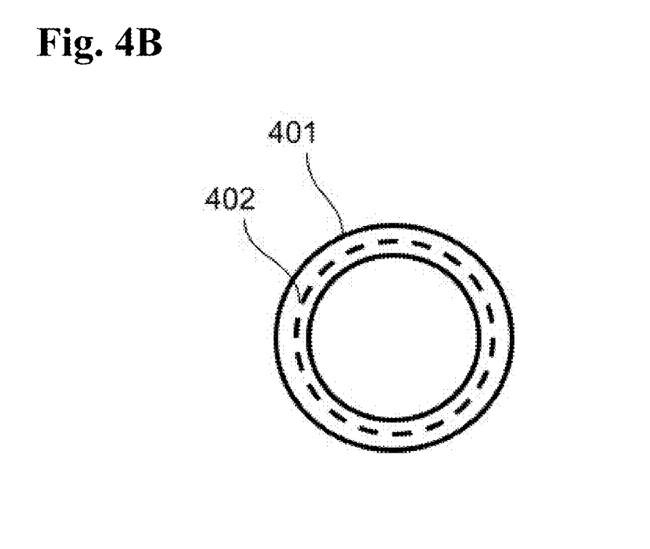

In the example depicted in FIGS. 2A-B first and second shapes, each of them is a circle. Alternatively the second shape can be a disk. The first shape can be referred to as target or "passive ring", while the second shape can be referred to as movable object or "active ring". Target 201 is stationary but changes its size on a permanent basis. Movable object (shape) 202 is thrown (moved) in the direction marked with the arrow, towards stationary target (shape) 201. An example of a modular logical structure of shapes 201 and 202 is schematically depicted in FIG. 2C. Stationary target 201 has resizing module 213 and switch 204 actuated by movable (thrown) object 202. In some examples switch 204 is actuated when movable object 202 reaches target 201 while geometrically fits to it. The actuation of switch 204 may stop the resizing of target 201 by module 213. Movable object 202 has movement module 205, resizing module 223, and a driving module 206. Driving module 206 is triggered as soon as the player has changed the size of movable object 202 by module 203 so that active ring 202 matches the size of passive ring 201, and directs movable object 202 towards stationary target 201. Switch 204 actuation occurs when thrown object 202 is encircled by stationary target 201 and at the same time corresponds to the dimensions of stationary target 201 as illustrated in FIG. 2B. The reader may understand that the modular logical structure example given in connection with shapes 201 and 202, is given here for illustration purposes only, does not depend on a particular geometry, and is applicable to a variety of shapes described herein by way of example, as well as other shapes which do not depart from the spirit of the present invention. The game shown as an example in FIG. 3A-B is similar to the game shown in FIGS. 2A-B in the difference that second shape 302 surrounds first shape 301 instead of the other way around. The example given in FIGS. 4A-B is similar to the examples in FIGS. 2A-B and 3A-B except first shape 401 consists of two concentric circles. The fit, in this case, is achieved when the player manages to place second shape 402 between the two concentric circles of first shape 401. For clarity, shape 402 is marked here with a dashed line.

The reader may understand that the examples given herein are for illustration only. For example, the shapes can be of a variety of types: polygons, rounded shapes, and three-dimensional shapes. The shapes can resemble sports such as ball games. The first shape can be a basket, goal, or pocket of a pool game. The second shape can accordingly be different types of balls, or a hockey disc ("puck"). In the case of bowling, the first shape will be a pin. In the case of billiard games the first shape can be a hole or a pocket, with the second shape being a ball. Another option is a kind of billiard game in which rings (tors) are used instead of balls and half rings instead of pockets. Alternatively, the first shape can be the ball, and the second form will be the stick (cue). Similarly, in hockey, the first shape can be either the goal or the puck while the second shape can be either the puck or the stick respectively. There may be cases where the two shapes, the first and the second, can move. For example in the case of tennis or badminton games, in which the bat moves toward the tennis ball itself in motion, or in the case of badminton the racquet and the shuttlecock respectively. Games that do not belong to well-known sports are also encompassed by the present invention, including invented/imagined sports. Shapes can be imaginary or be taken from or inspired by a variety of fields, such as warfare, aviation, transportation, wildlife, astronomy, science fiction, mythology, and fantasy.

Figure 5:
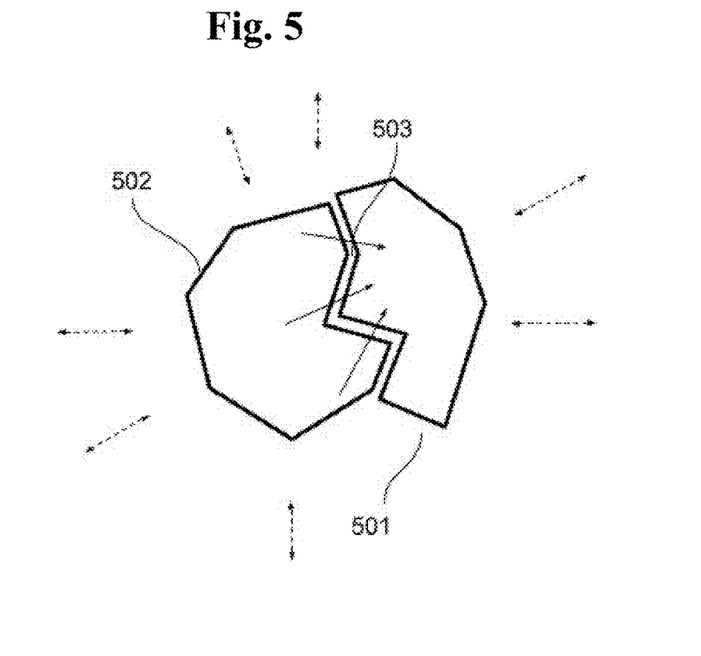
FIG. 5. illustrates schematically a game according to some embodiments of the invention where there is an importance for the direction of approachment of one shape to the other FIG. 6. illustrates schematically a game according to some embodiments of the invention with complex shapes FIG. 7. illustrates schematically a game according to some embodiments of the invention with three dimensional shapes FIG. 8. illustrates schematically a game according to some embodiments of the invention which includes maneuvering one of the shapes between barriers placed on the way to the other shape
Figure 6:
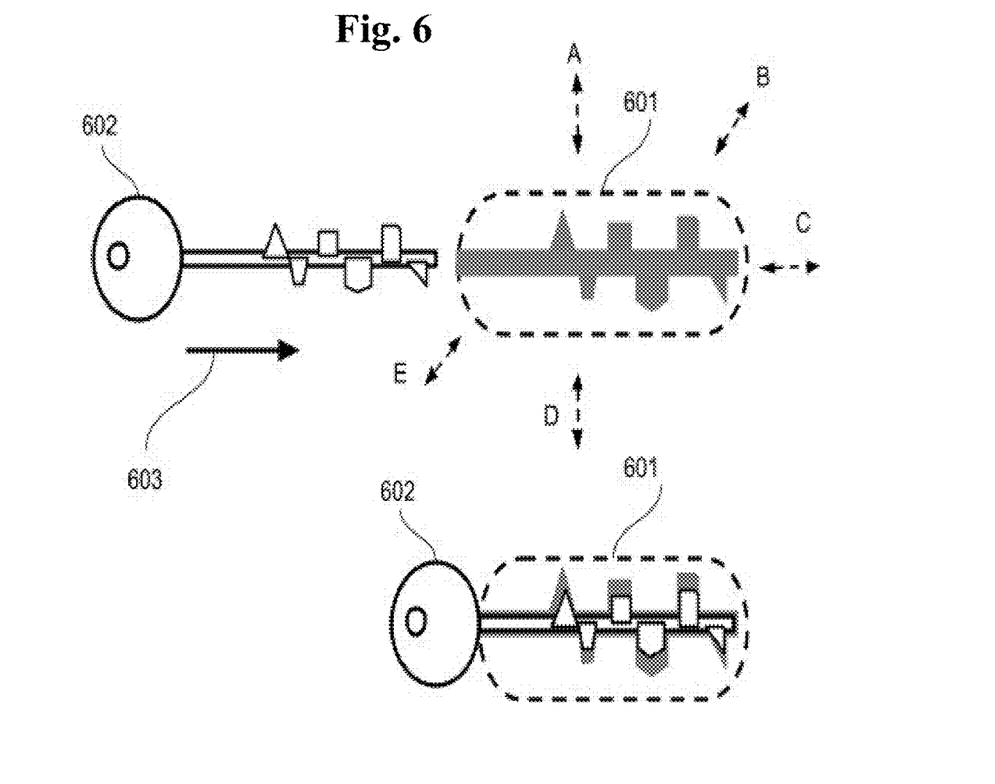
Figure 7:
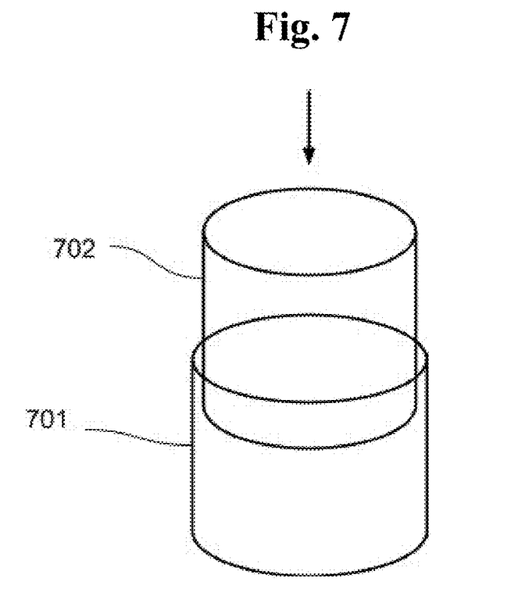
Figure 8:
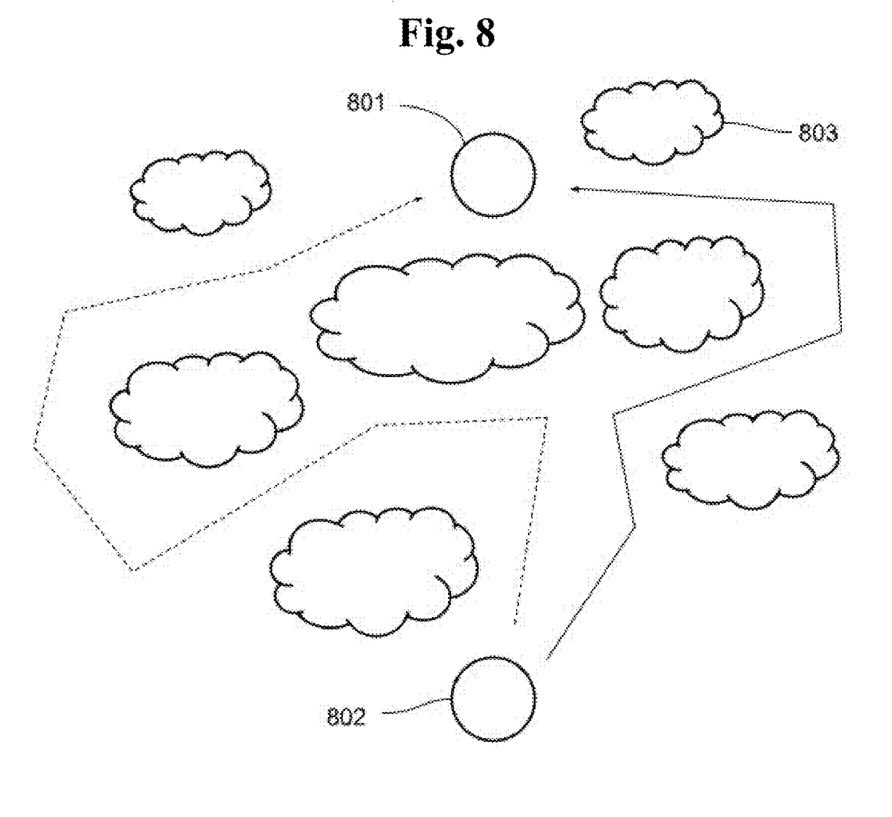

The example shown in FIG. 5 is of two polygonal shapes 501 and 502. The shapes complement each other in area 503. It can be seen that this case is sensitive to the direction of approachment of second shape 502. Possible directions of arrival of shape 502 are marked by continuous arrows. The dashed arrows come to illustrate possible directions of resizing. Because the shapes are not symmetrical, there is meaning to the direction that the size change is done in a way that requires more attention on the part of the player and there are more possibilities for mismatch between the shapes. That is, there is a greater challenge here in matching the shapes. Another challenge in the game is to accurately bring second shape 502 next to first shape 501 to a part of shape 501 that looks to the player as complement to second shape 502. The first shape may include different areas that look similar at first glance, but only one of them really fits the second shape. It is possible that the match test between the shapes will be performed only after receiving input from the player in which the player initiates a match check. FIG. 6 schematically depicts an example with complex shapes reminiscent of a lock (first shape) and a key (second shape). The direction of movement of key 602 towards lock 601 is depicted by continuous arrow 603. Similar to the example in FIG. 5 are resizing directions in dashed lines A-E. FIG. 7 is intended to illustrate a game according to embodiments of the invention that includes three-dimensional shapes 701 and 702. The direction of movement required for shapes matching is marked with an arrow. The example in FIG. 8 schematically illustrates a game involving additional complexity related to the movement of second shape 802 toward first shape 801 due to barriers 803 located between the two shapes. Two possible paths for moving shape 802 are marked with arrows. Not only does moving shape 802 on a complex path require additional attention from the player, another challenge is finding the fastest path in order to gain a high score when the score includes the speed in which matching between the shapes is achieved or in case the score is calculated according to the number of matches achieved at a given time. In some examples, the barriers move to make it even more difficult to select the path and move shape 802.

Figure 9A:
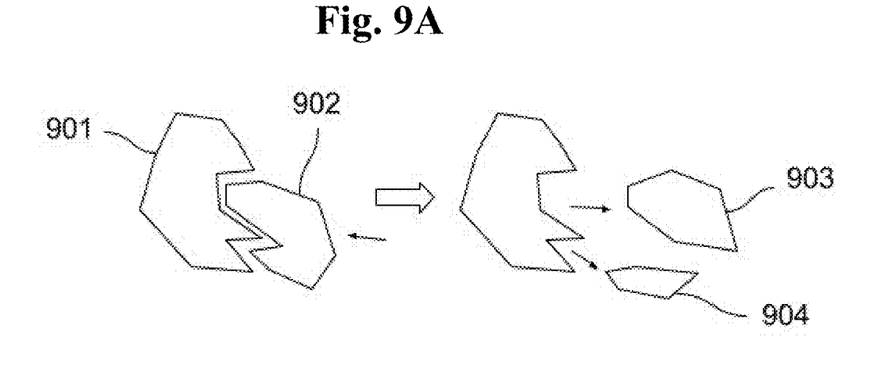
FIG. 9A depicts a substrate with spatial matching to an enzyme, decomposing into two products.
Figure 9B:
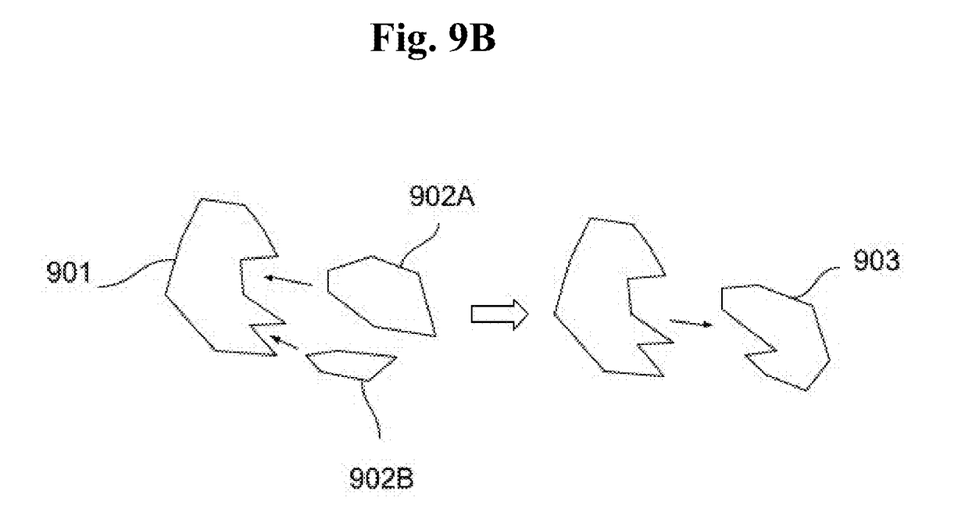
FIG. 9B shows two substrates bind following binding to an enzyme.
Figure 9C:
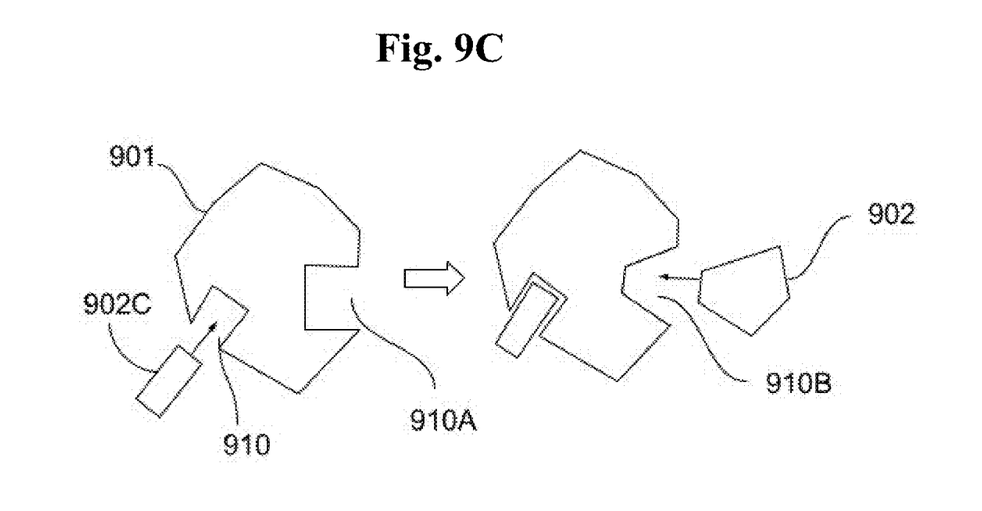
FIG. 9C depicts an induced fit where the region of attachment between the enzyme and the substrate undergoes a change to allow the matching between the enzyme and the substrate.
Figure 9D:
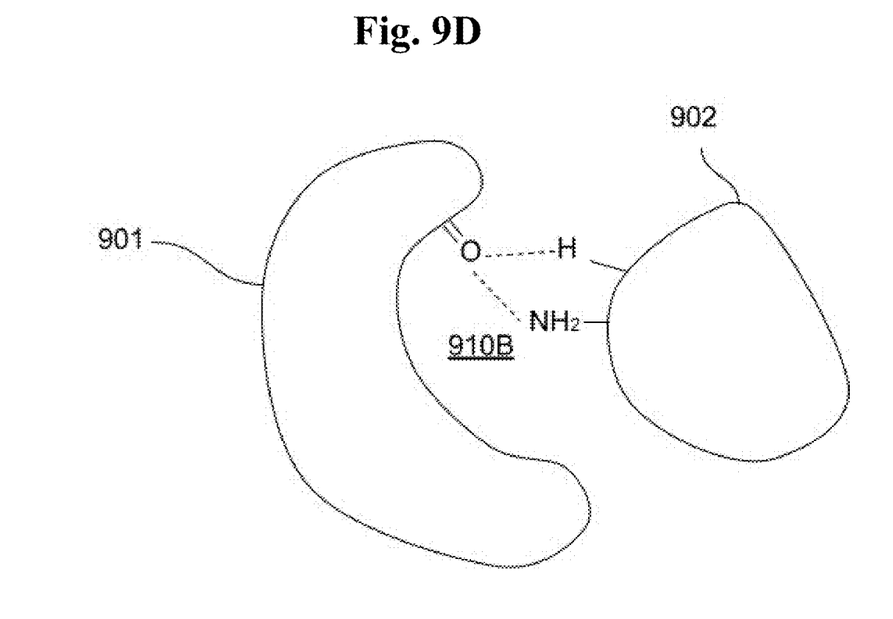
FIG. 9D shows two possible hypothetical chemical bonds between an enzyme and a substrate

One of the interesting scientific areas that can form the background for an educational game in the spirit of the present invention is enzymology. According to some embodiments of the invention, the processor is capable of receiving input from a database or memory device that includes the spatial structure of molecules of enzymes and substrates. In some examples, the processor may use the input of a user. Input from a user may include attempts of a user to in silico build known enzyme molecules from its smaller building blocks e.g., atoms, aromatic derivatives and functional groups. Such input may include a user's attempts to restore a known enzyme molecule based on data on substrates. Other more bold attempts may be for designing new unknown enzyme molecules based on data related to target substrates and functions. According to some examples the user can select chemical building groups, and chemical bonds from a menu presented to him or her, using a display device, in the form of a list or an acceptable graphic presentation of these building blocks. Without going into to much details a typical enzymatic reaction can be described as follows:

Some hypothetical examples of spatial matching from the field of enzymology are shown in FIGS. 9A-D. Those skilled in the field of enzymology are probably aware that the shapes constitute a simple schematic representation of a spatial structure determined by the molecular structure of the enzyme or substrate. More detailed spatial structures can be used to more closely represent the approximate structure of the enzyme or substrate. In FIGS. 9A-D, the enzyme is arbitrarily referred to as first shape 901, and the substrate as second shape 902. FIG. 9A illustrates an example of a case where substrate 902, with a successful spatial matching to enzyme 901, decomposes into two products 903 and 904. FIG. 9B shows an example in which two substrates 902A and 902B bind following binding to enzyme 901 to which they have a spatial adaptation, and become product 903. For those in the field of enzymology and biochemistry, they are aware that the affinity created between the enzyme and the substrate involves chemical reactions and catalysis related to the functionality of the enzyme as represented in the above basic chemical equation. These chemical processes involve the formation or decomposition of chemical bonds. Another hypothetical example is shown in FIG. 9C which schematically describes a case related to the induced fit theory. This theory includes a variety of situations in which the region of attachment between the enzyme and the substrate undergoes a change before to allow the matching between the enzyme and the substrate. In the example in FIG. 9C there is initially no match between enzyme 901 and substrate 902. Only after successful fit between activator 902C which matches site 910 in enzyme 901, site 910A in enzyme 901, undergoes a change and becomes a binding site 910B with fit to substrate 902. That is, the user must create a match, first between activator 902C and site 910, and only then will a match between substrate 902 and enzyme 901 be possible. FIG. 9D shows an option for presenting details related to the 910B site in enzyme 901. As noted above the affinity formed between enzyme 901 and substrate 902 commonly involves the formation of chemical bonds, two possible hypothetical ones being schematically depicted for illustration in FIG. 9D. The above examples from the field of enzymology were brought for the purpose of illustration, one of a possible variety according to the spirit of the present invention, of the possibility of advancing learning objectives through an experience of an enjoyable game.

In various embodiments the processor is adapted to allow communication among a plurality of players to provide a group gaming environment. In certain such embodiments, the processor enables players to work in conjunction with one another, such as by enabling the players to play together as a team or group, to win one or more awards. In other such embodiments, the processor enables players to compete against one another for one or more awards. In one such embodiment, the processor enables the players to participate in one or more gaming tournaments for one or more awards.

Figure 10A:
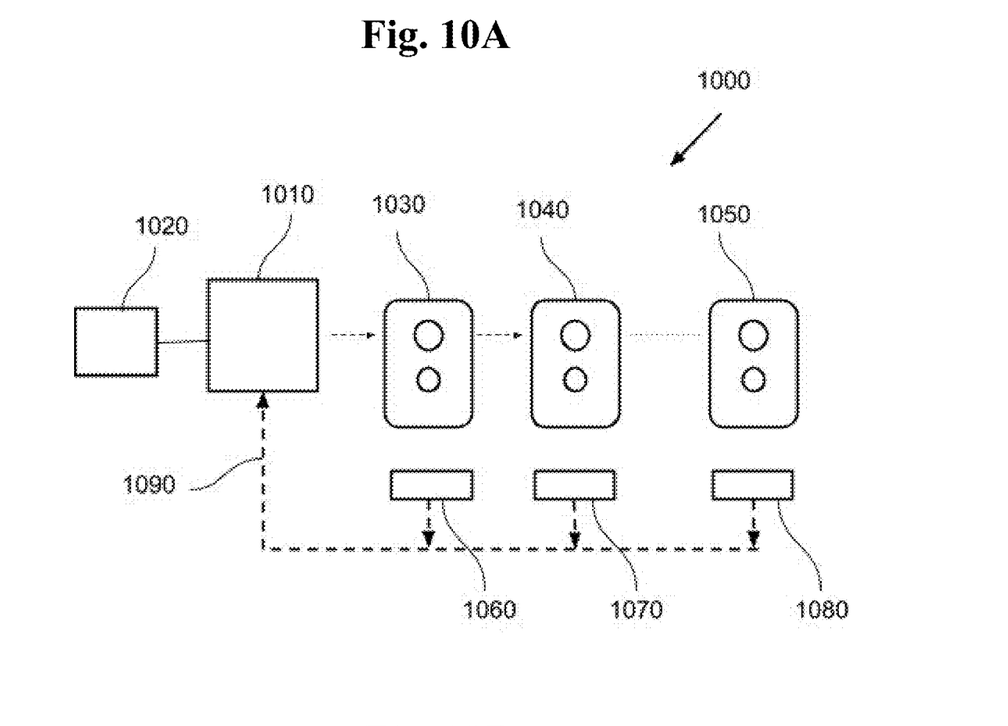
FIGS. 10A-B illustrate schematically multiplayer game systems according to some embodiments of the invention, where in the system depicted in FIG. 10A the competitors observe the shapes and their movements each in their own display in their turn; while in the system depicted in FIG. 10B the shapes being displayed simultaneously to multiple competitors In order to leave no room for doubt, the elements shown in the illustrations of the present patent application are presented in a manner that enables understanding them clearly, and the scales, size relations, and shapes are not in any way limiting their embodiment.
Figure 10B:
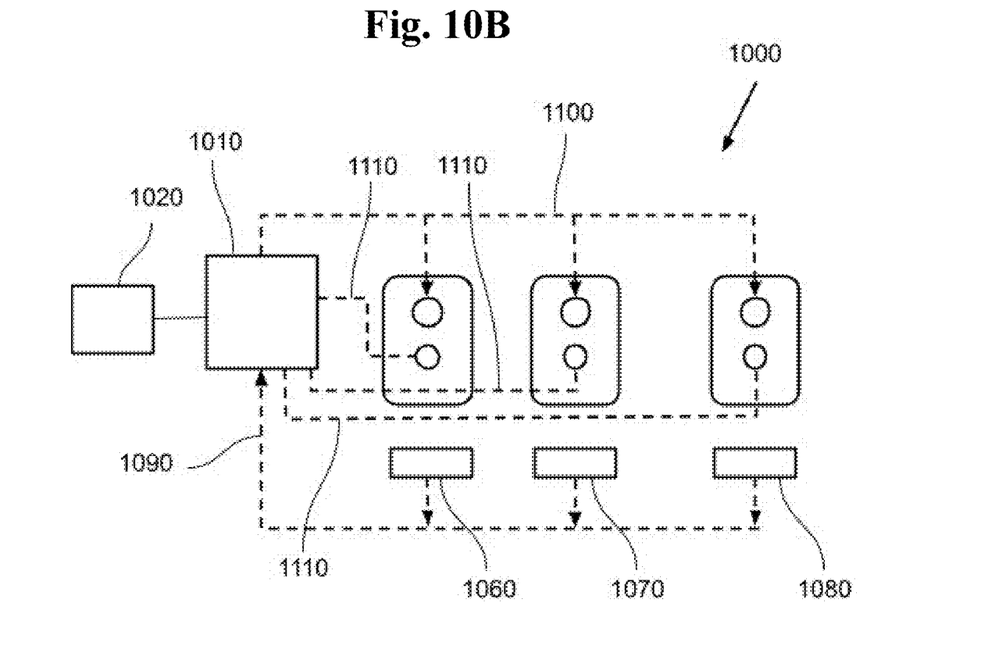

Competition between players can occur when each player in turn tries to match the second shape to the first shape. Another example is when a number of players are trying simultaneously to match each, his/her own second shape to a single first shape presented at the same time to all players. A possible criterion for winning a game can be the largest number of times a player has been able to match the second shape to the first shape. Another criterion can be the speed at which a successful match is made between the two shapes. The two criteria can be combined in such a way that victory is achieved according to a score that includes a weighting of the number of times a match between the shapes was achieved, as well as the average length of time in which a match had been achieved in all matching attempts that were successfully completed by a particular player. In some examples it may be that a successful attempt to match the shapes will result in the end of a game and the start of a new game. In other examples it may be that even if a successful match was achieved by one of the players, the game still continues so the other participants continue to try to match, each his/her own second shape to the first common shape. The game can continue according to several examples, until the last participant was able to match his/her second shape to the first shape. According to other examples, each game will be limited in time, so that the participants who manage to achieve a match will not have to wait until the last participant manages to get a match between the shapes. It should be noted that the examples are given herein for illustration by way of example, and in no way are intended to limit the scope of the invention. Examples of multiplayer gaming systems 1000 embodying the invention are schematically depicted in FIGS. 10A-B. System 1000 shown in FIG. 10A includes processor 1010 communicatively coupled to memory device 1020 that stores instructions executed by processor 1010. Processor 1010 is communicatively coupled to display devices 1, 2, to "n", indicated by numerals 1030, 1034, and 1050, respectively. Competitors 1 to "n", not shown, can observe the first and second shapes and their movements using display devices 1 to "n", each in its own turn in which he or she tries to match between the two shapes such as in the ways described above. Input from competitors 1090 comes from input devices 1,2 to n marked by numerals 1060, 1070, and 1080 respectively. The score or award each competitor receives in turn is calculated in processor 1010 according to the success achieved in matching the two shapes. The score or award is stored in memory device 1020. At the end of the game, processor 1010 sums up the scores or awards obtained by each of the players in all turns. The example shown in FIG. 10B is similar to that discussed in FIG. 10A except for the matter of showing the shapes. Instead of the shapes being displayed to a competitor in his or her turn each time, the display is made simultaneously to multiple competitors. Here the same first shape is presented to a number of competitors, while each competitor is presented with his or her second shape which he or she has to match to the first shape. In one option, all competitors can simultaneously watch the second shape of all the other competitors and the attempts of the other competitors to fit, each one, his or her own second shape to the common first shape. In another option, each competitor can see the common first shape but cannot watch the second shapes of other competitors. In FIG. 10B the common display of the first shape is represented by dashed line 1100, while the displays of the second shapes 1 to n are represented by dashed line 1110. Multiplayer games can also include an option where the first shape for one player would be the second shape for another player.

Numerous other changes, substitutions, variations, and modifications may be ascertained by the skilled in the art and it is intended that the present invention encompass all such changes, substitutions, variations and modifications as falling within the scope of the appended claims.

Further, one skilled in the art will recognize that functional units in this description have been labeled as modules throughout the specification. The person skilled in the art will also recognize that a module may be implemented as circuits, logic chips or any sort of discrete component. Still further, one skilled in the art will also recognize that a module may be implemented in software which may then be executed by a variety of processor architectures. In embodiments of the invention, a module may also comprise computer instructions or executable code that may instruct a computer processor to carry out a sequence of events based on instructions received. The choice of the implementation of the modules is left as a design choice to a person skilled in the art and does not limit the scope of this invention in any way.

Further, it should be understood that elements and/or features of a composition, an apparatus, or a method described herein can be combined in a variety of ways without departing from the spirit and scope of the present teachings, whether explicit or implicit herein. For example, where reference is made to a particular structure, that structure can be used in various embodiments of apparatus of the present teachings and/or in methods of the present teachings, unless otherwise understood from the context. In other words, within this application, embodiments have been described and depicted in a way that enables a clear and concise application to be written and drawn, but it is intended and will be appreciated that embodiments may be variously combined or separated without parting from the present teachings and invention(s). For example, it will be appreciated that all features described and depicted herein can be applicable to all aspects of the invention(s) described and depicted herein.

It should be understood that the expression "at least one of" includes individually each of the recited objects after the expression and the various combinations of two or more of the recited objects unless otherwise understood from the context and use.

The use of the term "include," "includes," "including," "have," "has," "having," "contain," "contains," or "containing," including grammatical equivalents thereof, should be understood generally as open-ended and non-limiting, for example, not excluding additional unrecited elements or steps, unless otherwise specifically stated or understood from the context.

The use of the singular herein, for example, "a," "an," and "the," includes the plural (and vice versa) unless specifically stated otherwise.

The use of any and all examples, or exemplary language herein, for example, "such as," "including," or "for example," is intended merely to better illustrate the present teachings and does not pose a limitation on the scope of the invention unless claimed. No language in the specification should be construed as indicating any non-claimed element as essential to the practice of the present teachings.

The present teachings encompass embodiments in other specific forms without departing from the spirit or essential characteristics thereof. The foregoing embodiments are therefore to be considered in all respects illustrative rather than limiting on the present teachings described herein.

The invention claimed is:

1. A gaming system comprising:
a processor; and
a memory device that stores a plurality of instructions that, when executed by the processor, cause the processor to:
cause a display, by at least one display device, of at least one first shape having a first location;
cause a display, by said display device, of at least one movable second shape having an initial location; and
receive, through at least one input device, at least one player command for dimensional change of said second shape, after which said second shape moves towards said first shape,
wherein said processor causes temporal dimensional changes of said first shape,
wherein at least one part of said second shape fits into at least one part of said first shape, at least in one temporary occurrence where said dimensions of said first shape and said second shape allow said fit,
wherein said processor checks whether said second shape reached said first shape, and
wherein said processor checks whether, if said second shape reached said first shape location there exists said fit.

2. The system of claim 1, wherein at least one of said first shape, and said second shape, comprises at least one empty inner zone.

3. The system of claim 1, wherein at least one of said first shape, and said second shape, is three dimensional.

4. The system of claim 1, wherein said processor is adapted to allow communication among a plurality of players and said processor, to provide a group gaming environment.

5. The system of claim 4, wherein said first shape of at least one player is said second shape for at least another player.

6. The system of claim 4, wherein said second shape of at least one player is said first shape for at least another player.

7. The system of claim 1, wherein said temporal dimensional changes of said first shape, caused by said processor, are at random time intervals.

8. The system of claim 1, wherein said processor provides an award each time said fit occurs.

9. A method of operating a gaming system, said method comprising:
causing a processor which causes at least one display device to display at least one first shape, said first shape having a first location;
causing said processor to cause at least one display device to display at least one second shape, said shape second having an initial location; and
receiving, through at least one input device, at least one player command for dimensional change of said second shape, after which said second shape moves towards said first shape,
wherein said processor causes temporal dimensional changes of said first shape,
wherein at least one part of said second shape fits into at least one part of said first shape, at least in one temporary occurrence where said dimensions of said first shape and said second shape allow said fit,
wherein said processor checks whether said second shape reached said first shape, and
wherein said processor checks whether, if said second shape reached said first shape location there exists said fit, said processor provides an award for each time said fit occurs.

10. The method of claim 9, wherein at least one of said first shape, and said second shape, comprises at least one empty inner zone.

11. The method of claim 9, wherein at least one of said first shape, and said second shape, is three dimensional.

12. The method of claim 9, wherein said processor is adapted to allow communication among a plurality of players and said processor, to provide a group gaming environment.

13. The method of claim 9, wherein said first shape of at least one player is said second shape for at least another player.

14. The method of claim 9, wherein said second shape of at least one player is said first shape for at least another player.

15. The method of claim 9, wherein said temporal dimensional changes of said first shape, caused by said processor, are at random time intervals.

16. The method of claim 9, comprising providing an award by said processor each time said fit occurs.

* * * * *